US00PP15781P3

(12) United States Plant Patent
Hammond

(10) Patent No.: US PP15,781 P3
(45) Date of Patent: Jun. 7, 2005

(54) ***CHRYSANTHEMUM* PLANT NAMED 'ESPERANTO IMPROVED'**

(50) Latin Name: *Chrysanthemum morifolium*
Varietal Denomination: Esperanto Improved

(75) Inventor: Richard Hammond, Gran Canaria (ES)

(73) Assignee: Aurora Varieties S.L. (ES)

( * ) Notice: Subject to any disclaimer, the term of this patent is extended or adjusted under 35 U.S.C. 154(b) by 155 days.

(21) Appl. No.: 10/677,474

(22) Filed: Sep. 23, 2003

(65) Prior Publication Data

US 2004/0093652 P1 May 13, 2004

Related U.S. Application Data

(60) Provisional application No. 60/413,584, filed on Sep. 24, 2002.

(51) Int. Cl.[7] ..... A01H 5/00
(52) U.S. Cl. ..... Plt./286
(58) Field of Search ..... Plt./286

(56) References Cited

U.S. PATENT DOCUMENTS

PP11,758 P2 1/2001 Vandenberg ..... Plt./286

2003/0121087 P1 6/2003 Hammond ..... Plt./286

OTHER PUBLICATIONS

2000 Ficor Catalog, published Nov. 9, 1999, listing *Chrysanthemum* variety 'Esperanto' under commercial name 'Esperanza.' See pp. 4 and 13.

2001 Ficor Catalog, published Oct. 12, 2000, listing *Chrysanthemum* variety 'Esperanto.' See pp. 2 (color photograph), 4 and 9.

2002 Ficor Catalog, published Sep. 25, 2001, listing *Chrysanthemum* varieties 'Esperanto' and 'Esperanto Improved.' See pp. 4, 9, 16 (color photograph) and unnumbered insert.

*Primary Examiner*—Anne Marie Grunberg
*Assistant Examiner*—June Hwu
(74) *Attorney, Agent, or Firm*—Howrey Simon Arnold & White, LLP

(57) ABSTRACT

A new variety of *Chrysanthemum* plant named 'Esperanto Improved,' having a uniform canopy of dark pink-purple/white striped single type flowers with a yellow/green disc. The new variety exhibits medium vigor with a free branching and uniform spreading habit and good foliage presentation.

1 Drawing Sheet

Latin name of the genus and species: Botanical classification: *Chrysanthemum morifolium.*

Variety denomination: The new *Chrysanthemum* variety denomination is 'Esperanto Improved.'

BACKGROUND OF THE INVENTION

The present invention comprises a new and distinct cultivar of *Chrysanthemum* botanically known as *Chrysanthemum morifolium,* and referred to by the cultivar name 'Esperanto Improved.'

'Esperanto Improved,' originated from a naturally occurring whole plant mutation grown in a controlled planting of the variety 'Esperanto' (U.S. Plant patent application Publication No. 2003/0121087) at Valsequillo, Gran Canaria, Spain. The new variety 'Esperanto Improved' has been asexually reproduced by vegetative cuttings in Chichester, West Sussex, United Kingdom and the distinguishing characteristics are retained through successive generations of asexual reproduction.

BRIEF SUMMARY OF THE INVENTION

'Esperanto Improved' is a pot type of *Chrysanthemum* plant variety having dark pink purple/white striped single type flowers.

Comparison with Parent

Plants of the new *Chrysanthemum* variety 'Esperanto Improved' are similar to the parent 'Esperanto' in plant habitat and growth rate. In side-by-side comparisons in Chichester, West Sussex, United Kingdom, under commercial practice, plants of the new *Chrysanthemum* variety 'Esperanto Improved' compared to plants of the parent 'Esperanto' in the following characteristics.

1. The new variety 'Esperanto Improved' produces dark pink-purple/white single type flowers whereas the parent 'Esperanto' produces paler pink/white striped single type flowers.
2. Plants of the new variety 'Esperanto Improved' have similar inflorescence to the plants of the parent 'Esperanto.'

BRIEF DESCRIPTION OF ILLUSTRATIONS

Typical specimens of the plant and flowers for the new *Chrysanthemum* variety 'Esperanto Improved' are shown in the accompanying digital photograph. The colors shown are as true as possible within the usual limits of this kind of illustration.

FIG. 1 is a whole plant view of the new variety 'Esperanto Improved' grown in a pot. The plant shown in the illustration and described here is 53 days from commencement of Short Days.

DETAILED BOTANICAL DESCRIPTION

The following description of the new *Chrysanthemum* variety 'Esperanto Improved' is of plants grown in a greenhouse in Chichester, West Sussex, United Kingdom in the month of February. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 18° C. at night and about 24° C. to 25° C. during the day under light conditions of about 5000 to 6000 foot candles. The plants respond well to the use of growth retardant, such as B9 treatment. To produce a commercial product the plants may be pinched once with the center bud removed. The typical container size for commercial growth is 14 cm. It has been observed that the shelf life of the new variety as a pot *Chrysanthemum* is about 24 days with a response time of about 7.5 weeks. The new variety is suitable for growth in a temperature range of 17° C. to 28° C.

The following description is with respect to a plant produced as pot *Chrysanthemum.* In the description of this new *Chrysanthemum* variety, color values have been taken from The Royal Horticultural Society Colour Chart (R.H.S.C.C.).

Plant

Plant type: Pot.
Habit: Upright and free branching.
Height: 23 cm.
Width: 36 cm.
Branching characteristics: Upright and free branching.
Length of lateral branches: 6–11 cm.
Number of breaks from pinch: 3–5.
Stem color: 137A.
Response time: 53 days.
Vigor: Medium.
Shelf life as a pot *Chrysanthemum:* 24 days.
Disease/pest (susceptibility/resistance observed): None observed to date.
Growth retardant type and treatment: 3 applications of 2.5 gm/liter B9 at 2, 21, and 28 days after sticking of unrooted cuttings.

The plants were grown for 3 weeks in Long Day conditions (20 hours of light) and then transferred to Short Day conditions (13 hours of dark).

Propagation:
*Type.*—Vegetative Propagation Via Stem Cuttings.
*Time to rooting.*—12–14 days with soil temperatures of 18° C.
*Rooting habit.*—Fine and Fibrous.

Foliage

Number of leaves per lateral branch: 8–11.
Compound or single: Single.
Arrangement of leaves: Alternate.
*Shape of leaf.*—Typically 5 lobed ovate.
*Size of leaf.*—Width (cm): 3.5–7. Length (cm): 5–10.
*Leaf apex.*—Acute.
*Base.*—Obtuse.
*Attachment.*—Petioled.
*Aspect.*—Slightly undulating.
*Margin.*—Palmetely lobed.
*Surface characteristics.*—Top: Slightly pubescent. Bottom: Pubescent.
Petiole:
*Color.*—137B.
*Length.*—1.5 cm.
*Diameter.*—0.2 cm.
*Surface.*—Slightly pubescent.
Venation: Net prominent midvein at underside.
*Color.*—Upper side: Near 146D. Under side: Near 146D.
Color:
*Mature leaf, upper side.*—Near 137A; under side: Near 138A.
*Young leaf, upper side.*—Near 137B; under side: Near 138B.

Flower

Flower appearance: Slightly cupped.
Flower type: Single.
Flower form: Cupped.
Flower shape: Circular.
Flowering habit: Cyme.
Number of blossoms per branch: 3–5.
Inflorescence form: Pyramidal.
*Depth of fully expanded blossoms.*—2 cm.
*Diameter of fully expanded blossoms.*—6–7 cm.
Phyllaries:
*Number.*—28–30.
*Outer color.*—Near 136C.
*Length.*—0.5–0.9 cm.
*Width.*—0.2–0.4 cm.
*Texture/appearance.*—Pubescent.
Peduncle: Peduncle length is shortest at the terminal flower and progressively longer moving down the stem.
*Length.*—2.5–10 cm.
*Color.*—Near 136C.
*Surface.*—Pubescent.
*Habit.*—Slightly curving.
*Strength.*—Medium.
*Diameter.*—0.15 cm.
Pedicel:
*Length.*—Terminal: 2–4.5 cm; Lateral: 2.5–7 cm.
*Color.*—Near 138B.
*Surface.*—Pubescent.
*Habit.*—Slightly curving.
*Strength.*—Medium.
Ray florets:
*Form/shape.*—Elliptic with a tapered tip.
*Texture/appearance.*—Matte.
*Number per flower.*—25–30.
*Length.*—3–3.5 cm; Width: 0.8–1.2 cm.
*Apex.*—Rounded.
*Base.*—Tubular.
*Margin.*—Entire.
Disc florets:
*Form/shape.*—Cylindrical.
*Texture/appearance.*—Shiny.
*Number per flower.*—170–250.
*Length.*—0.3–0.6 cm; Width <0.1–0.1 cm.
*Diameter of disc.*—1.2–1.5 cm.
Fragrance: Faint.
Flower bud (at onset of color):
*Length.*—1.5 cm.
*Diameter.*—1.0 cm.
*Form/shape.*—Globular.

General flower color:

1. *Ray florets, upper side.*—Immature: About 50% near 58B and about 50% 155D in a lengthwise striped pattern. Mature: About 50% near 58B and about 50% 155D in a lengthwise striped pattern. Older/Fading: About 50% near 58C and about 50% 155D in a lengthwise striped pattern.
2. *Ray florets, under side.*—Immature: About 50% near 58B and about 50% 155D in a lengthwise striped pattern. Mature: About 50% near 58B and about 50% 155D in a lengthwise striped pattern. Older/Fading: About 50% near 58C and about 50% 155D in a lengthwise striped pattern.
3. *Disc florets.*—Immature: Near 143B. Mature: Near 154B. Older/Fading: Near 143A.
4. *Bud.*—138B.

Flower progression with age: Flower form does not change with age but there is a little color fading.

Other distinguishing characteristics: Foliage remains good with age.

Reproductive Organs

Gynoecium present on Ray and Disc florets.

*Ray florets.*—
*Pistil number:* 25.
*Stigma color.*—Near 6C.
*Stigma shape.*—Forked.
*Style color.*—Near 6C.
*Style length.*—0.4 cm.
*Disc florets.*—
*Pistil number:* 60–75.
*Stigma color.*—Near 6C.
*Stigma shape.*—Forked.
*Style color.*—Near 6C.
*Style length.*—0.2 cm.

Androecium: None observed to date.

Fruit and seeds: None observed to date.

What is claimed is:

1. A new and distinct variety of *Chrysanthemum* plant, substantially as described and illustrated herein.

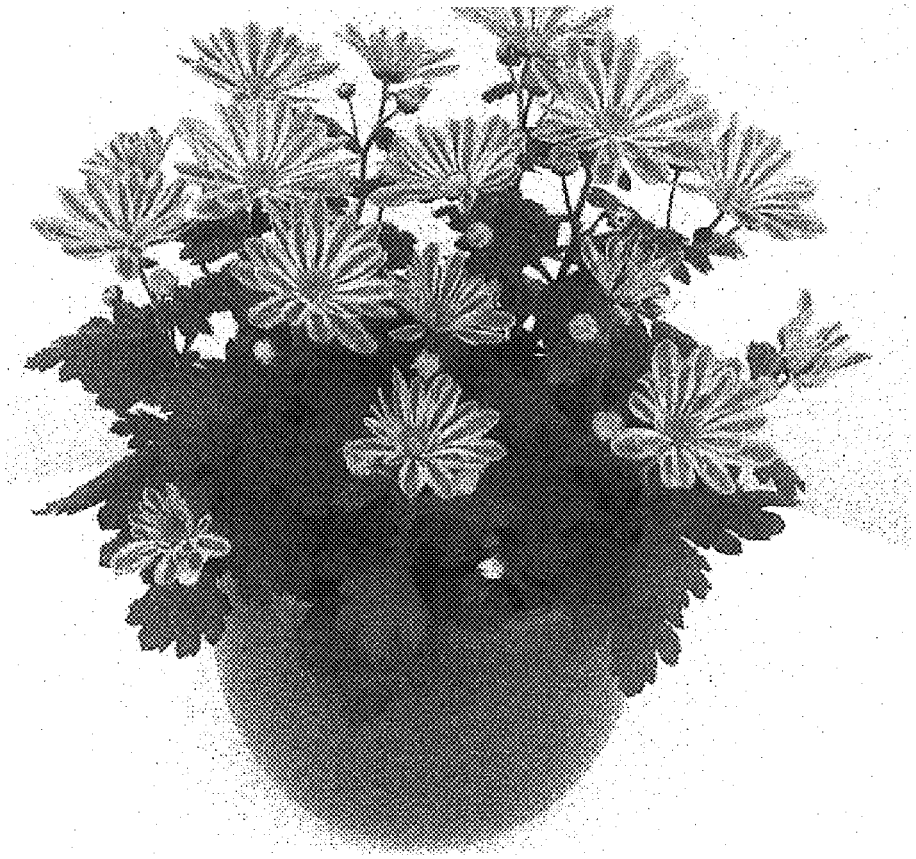

* * * * *